United States Patent [19]

Fung et al.

[11] Patent Number: 4,548,809

[45] Date of Patent: Oct. 22, 1985

[54] METHOD FOR MANUFACTURING A STOMATIC GARGLE

[76] Inventors: Paul S. T. Fung, Ste. 1406, No. 185, Sung Chiang Rd.; Yun-Tsu Chen, No. 3, Alley 18, La. 64, Nanking W. Rd., both of Taipei, Taiwan

[21] Appl. No.: 594,486

[22] Filed: Mar. 27, 1984

[51] Int. Cl.[4] .................. A61K 7/16; A61K 7/18; A61K 7/26
[52] U.S. Cl. ...................... 424/52; 424/49; 424/58
[58] Field of Search ................... 424/49–58

[56] References Cited

U.S. PATENT DOCUMENTS

| | | | |
|---|---|---|---|
| 1,488,097 | 3/1924 | Creger | 424/58 |
| 2,769,011 | 10/1956 | Hacker | 424/49 |
| 2,773,802 | 12/1956 | Gruskin | 424/57 |
| 2,783,182 | 2/1957 | Nelson | 424/57 |
| 2,815,314 | 12/1957 | Hale | 424/58 |
| 3,720,762 | 3/1973 | Hatasa | 424/58 |
| 4,150,151 | 4/1979 | Pader et al. | 424/56 |
| 4,420,471 | 12/1983 | Elton et al. | 424/58 |
| 4,423,030 | 12/1983 | Hayes et al. | 424/58 |
| 4,430,323 | 2/1984 | Silver | 424/52 |
| 4,469,673 | 9/1984 | Lioka et al. | 424/58 |

FOREIGN PATENT DOCUMENTS

| | | | |
|---|---|---|---|
| 964499 | 1/1950 | France | 424/58 |
| 56-83416 | 8/1981 | Japan | 424/58 |
| 57-38708 | 3/1982 | Japan | 424/58 |
| 57-56416 | 5/1982 | Japan | 424/58 |
| 58-55409 | 1/1983 | Japan | 424/58 |
| 58-57320 | 5/1983 | Japan | 424/58 |
| 59-13712 | 1/1984 | Japan | 424/58 |
| 240182 | 7/1969 | U.S.S.R. | 424/58 |

Primary Examiner—Shep K. Rose
Attorney, Agent, or Firm—Wenderoth, Lind & Ponack

[57] ABSTRACT

A method for manufacturing a stomatic gargle, which is prepared with three kinds of liquids, i.e., liquid A made of very small quantities of menthol, eugenol and eucalyptus oil which are dissolved in ethyl alcohol; liquid B made of licorice extract dissolved in a warm distilled water; liquid C made of sodium monofluorophosphate and sodium fluoride added to distilled water at a temperature of 30° C. with agitation. The liquid C is added to liquid B, a very small quantity of glycerol, perfume, non-ionic surfactant and sodium dehydroacetate, and are agitated at a low speed for 3 to 7 minutes. A very small quantity of perfume and flavor additives is then added. Then slowly liquid A is added to the mixed liquid with distilled water, ethylalcohol and a very small quantity of chlorophyll so as to obtain a transparent and green gargle.

5 Claims, No Drawings

METHOD FOR MANUFACTURING A STOMATIC GARGLE

BACKGROUND OF THE INVENTION

The stomatic sanitation has long been a concern of the public; particularly, in today's society, where people's living standards (or quality) have been lifted considerably. The general public takes high molecular protein meat or other kind of acid meat as their main foods. The acid residues of such foods being left between the teeth and the gums not only can give rise to bacteria that cause the mouth to feel dry and halitosis, but also can cause a cavities and gingivitis or bleeding gums, etc. Such stomatic diseases have bothered the public and the dentists since long ago. Both the chemical industries and other industrial circles have continuously provided various kinds of tooth brushes, tooth pastes, tooth powder and stomatic cleaning apparatus; however, none of the aforesaid means can provide better cleaning and bactericide effects than gargle. Unfortunately, the ordinary and current gargles have a pepper hot flavor and stimulant effect, and they would make the user's stomatic area feeling numb. Upon gargling, the stomatic area and the tongue will lose their sense of taste for a short period time. Such features of the current gargles have put consumers to some inconveniences; therefore, some consumers refrain from using it.

SUMMARY OF THE INVENTION

In view of the drawbacks of the ordinary and current gargles, the inventor has developed a method for manufacturing a stomatic gargle which can thoroughly clean the acid residues between the teeth, kill the bacteria in the mouth and throat, prevent the teeth from having cavities and the gums from gingivitis or bleeding, remove the halitosis and dry feeling in the mouth and throat so as to maintain one's mouth always in a clean state.

Another feature of the present invention is to provide a green, cool, fragrant, and sweet flavored gargle.

A still another feature of the present invention is to provide a gargle which is safe and acceptable for human consumption and for the sense of smell without any having a stimulant nature.

A further feature of the present invention is to provide a gargle that may be stored for long time after being sterilized through high temperature sterilization.

A still further feature of the present invention is to provide a gargle which can be manufactured without using too much investment and technical knowledge and skills.

A still further feature of the present invention is to provide a gargle that contains the ingredients of chlorophyll, eucalyptus oil, and licorice, etc., and that has the potencies of soothing the stomatic skin, of protecting the throat suffering from diseases.

DETAILED DESCRIPTION OF THE PREFERRED EMBODIMENT

This invention relates to a method for manufacturing a stomatic gargle, which was developed by the inventor through many years of study. The precedures of this method is first to prepare three kinds of liquids, i.e., liquid A, B, and C. Liquid A is to be prepared with menthol ($C_{10}H_{19}OH$), a very little quantity of eugenol ($C_3H_5C_6H_3(OH)OCH_3$) and some eucalyptus oil equal to 10 times the quantity of menthol, being all added and dissolved in ethyl alcohol ($C_2H_5OH$). Among the aforesaid ingredients, the menthol is a white crystal structure, having menthol fragrance and having local anaesthetic, antiseptic, and repellent potencies; the eugenol is a colorless or very light yellow oil which is a bactericide and a perfume, and which is also a good medicine for curing tooth-ache; eucalyptus oil is a colorless or light yellow perfume oil that can provide a cool and comfortable smell, and its main components are phellandrane, eucalyptol, citral and piene. The eucalyptus oil may be obtained by distilling the fresh eucalptus leaves, which are then washed with sodium hydroxide and are re-distilled. The eucalyptus oil has bactericidal, repellent, and sterilizing effects. Ethyl alcohol is a colorless liquid, having ether flavor and bactericide and antiseptic effects. Ethyl alcohol is used as a solvent in liquid A, since the menthol, eugenol, and the eucalyptus oil can all be dissolved in ethyl alcohol.

Liquid B is made from licorice, which is a bean family plant with a small blue flower, and which contains a licorice extract having a sweet and fragrant flavor and being used as a medicine; further, the licorice extract has the properties of neutralizing toxin, reducing greasy, and soothing one's throat; therefore, it is one of the good medicines in curing throat diseases. In preparing liquid B, the licorice is dipped in distilled water at a temperature of 100° C. so as to let the licorice extract dissolve completely in the distilled water; then, the distilled water is screened with a filter for removing the licorice residues for obtaining a pure liquid B.

Liquid C may be prepared by dissolving a suitable quantity of sodium mono-fluorophosphate into distilled water at a temperature of 30° C., and agitating it until it is dissolved completely; then, sodium fluoride is added in the same weight as the sodium mono-fluorophosphate into the liquid and agitated until it is dissolved completely. At that time, the liquid C is ready for use. Since both the sodium fluoride and the sodium mono-fluorophosphate have the effects of bactericide and sterilizing, and are a little bit toxic in nature, the contents thereof in the liquid must be rigidly controlled. At the most, the aforesaid chemicals must not be more than 0.5% of the total dosage of the gargle so as not to jeopardize a user's health.

Upon the aforesaid liquids being ready, liquid B is heated at a temperature ranging from 30° C.–50° C., preferably at 40° C.; then, liquid B is poured into liquid C, and a suitable quantity of glycerol (($CH_2OH)_2$-$CHOH$), perfume, non-ionic surfactant, and sodium dehydroacetate, etc., is added and the combination agitated at a low speed (under 300 RPM) for about 3 to 7 minutes, preferably 5 minutes. Then, liquid A is added to the mixed liquid, and simultaneously a very small quantity of perfume and flavor additives is added, and then the mixed liquid is agitated into a suspension and turbid liquid. In that turbid liquid, the glycerol is colorless or light yellow julep without odour and the perfume will provide the gargle with a cool and fragrant flavor. The non-ionic surfactant in the gargle of the present invention is a main component of synthetic washing detergent, which can reduce the surface tension of liquid. In the gargle of the present invention, "Dodecyl diethylenetriamine" is used as the non-ionic surfactant to provide a better cleaning effect.

In the aforesaid suspension and turbid liquid, a suitable quantity of distilled water or ethyl alcohol may be added slowly since distilled water and ethyl alcohol are good solvents, which can gradually cause the mixed liquid to become clear and transparent. Further, the mixed liquid may also be supplemented with a suitable quantity of chlorophyll ($C_{55}H_{72}O_5N_4Mg$), which can change the gargle into a green liquid, which is preferred by consumers. Since chlorophyll is a nutritious stuff, it can protect the skin film in one's mouth, and can soothe one's throat.

The gargle made by the aforesaid method may be sterilized by means of a high temperature steam means for longer storage time without deteriorating, or for immediate packing for sale in the market. This gargle may satisfy a rigid and long expected requirement of the public for stomatic sanitation.

The following embodiment will provide the percentages of each of the chemical ingredients of the gargle; however, it does not follow that the claims of the present invention will be confined by the embodiment.

| Embodiment | |
|---|---|
| Ingredients | Percentages |
| Chlorophyll | 0.001% |
| Sodium monofluorophosphate | 0.250% |
| Sodium fluoride | 0.250% |
| Menthol | 0.200% |
| Eugenol | 0.040% |
| Licorice | 0.300% |
| Glycerol | 3.000% |
| Ethylalcohol | 40.000% |
| Perfumes | 0.500% |
| Non-Ionic surfactant | 0.025% |
| Sodium dehydroacetate | 0.040% |
| Distilled water | 53.394% |
| Eucalyptus oil | 2.000% |

Any other method that does not deviate from the novel concept and spirit of the present invention, but is a minor change in the method is deemed to fall within the scope of the claims of the present invention.

We claim:

1. A method of manufacturing a stomatic gargle, comprising the steps of:
   (1) forming a first liquid mixture including a small quantity of menthol effective to function as a fragrance, local anaesthetic and antiseptic the user's mouth, a very small quantity of eugenol, less than that of the menthol, effective to function as a bactericide, a pain killer and a light anaesthetic agent in the user's mouth, and
   a quantity of eucalyptus oil approximate 10 times that of the menthol, effective to function as an antiseptic and bactericide in the user's mouth;
   (2) dissolving a quantity of licorice effective to function as a sweetener, into a first quantity of 100° C. distilled water sufficient to dissolve the licorice, and passing the dissolved licorice and water through a filter to remove licorice residues to produce a second liquid mixture;
   (3) adding a small quantity of sodium monofluorophosphate effective to function as a sterilizing agent and antiseptic agent for eliminating bacteria in the mouth to a second quantity of 30° C. distilled water effective to dissolve the sodium monofluorophosphate, and agitating the water and sodium monofluorphosphate until disolution is complete to produce a third liquid mixture;
   (4) adding the second liquid mixture at a temperature in the range 30° C. to 50° C. to the third liquid mixture to form a fourth liquid mixture;
   (5) adding a quantity of glycerol effective to increase viscosity, a very small quantity of perfume effective to provide a cool and fragrant flavor to the gargle, a very small quantity of non-ionic surfactant effective to function as cleanser in the mouth and reduce surface tension in the gargle, and a quantity of sodium dehydroacetate effective to function as a water softening agent, to the fourth liquid mixture to form a fifth liquid mixture;
   (6) agitating the fifth mixture for about 3 to 7 minutes at a slow speed under 300 RPM to form a sixth liquid mixture;
   (7) adding the first liquid mixture, and a very small quantity of perfumes and flavor additives effective to add a cool flavor to the gargle to the sixth liquid mixture to form a seventh liquid mixture;
   (8) agitating the seventh liquid mixture until the seventh liquid mixture forms a turbid suspension; and
   (9) adding sufficient quantities of distilled water, ethyl alcohol and chlorophyll to the turbid suspension to obtain a clear transparent green gargle.

2. A method as in claim 1, wherein the total quantity of said sodium monofluorophosphate and sodium fluoride is no greater than 0.5% of the total quantity of said gargle.

3. A method as in claim 1, wherein the quantity of ethyl alcohol is about 35% to 45% of the total quantity of said gargle.

4. A method as in claim 1, wherein the total quantity of the distilled water is about 45% to 60% of the total quantity of said gargle.

5. A method as in claim 2, wherein the quantity of ethyl alcohol is about 35% to 45%, and the total quantity of the distilledwater is about 45% to 60%, of the total quantity of said gargle.

* * * * *